United States Patent
Griffin et al.

(10) Patent No.: US 9,869,637 B2
(45) Date of Patent: Jan. 16, 2018

(54) RADIOACTIVE ANOMALY DETECTOR

(71) Applicant: Raytheon Company, Waltham, MA (US)

(72) Inventors: Eric J. Griffin, Rancho Palos Verdes, CA (US); Kalin Spariosu, Thousand Oaks, CA (US); Erik D. Johnson, Boston, MA (US)

(73) Assignee: RAYTHEON COMPANY, Waltham, MA (US)

( * ) Notice: Subject to any disclaimer, the term of this patent is extended or adjusted under 35 U.S.C. 154(b) by 382 days.

(21) Appl. No.: 14/733,433

(22) Filed: Jun. 8, 2015

(65) Prior Publication Data

US 2016/0356714 A1    Dec. 8, 2016

(51) Int. Cl.
*G01N 21/63*    (2006.01)
*G01N 33/00*    (2006.01)
(Continued)

(52) U.S. Cl.
CPC ............ *G01N 21/63* (2013.01); *B66C 1/101* (2013.01); *B66C 13/18* (2013.01); *B66C 19/002* (2013.01); *G01J 3/0291* (2013.01); *G01J 3/443* (2013.01); *G01N 1/2226* (2013.01); *G01N 15/1459* (2013.01); *G01N 21/25* (2013.01); *G01N 21/6404* (2013.01); *G01N 21/718* (2013.01); *G01N 33/004* (2013.01); *G01N 33/0057* (2013.01); *G01V 5/0091* (2013.01); *G06Q 10/083* (2013.01); *B64F 1/32* (2013.01); *B64F 1/368* (2013.01); *G01N 1/24* (2013.01); *G01N 2015/0046* (2013.01); *G01N 2021/6406* (2013.01); *G01N 2201/06113* (2013.01)

(58) Field of Classification Search
CPC .. G01N 21/63; G01N 21/6404; G01N 21/718; G01N 1/2226; G01N 21/25; G01N 33/004; G01N 33/0057; G01N 2021/6406; G01N 2201/06113; G01V 5/0091; G01J 3/443
See application file for complete search history.

(56) References Cited

U.S. PATENT DOCUMENTS 5,751,416 A * 5/1998 Singh .................... G01J 3/30
    356/300
7,945,108 B2 * 5/2011 Kono ................. G01N 21/6458
    359/391

(Continued)

OTHER PUBLICATIONS

ISR/WO, Issued Jun. 28, 2016, PCT/US2016/026319, 16 pages.

(Continued)

*Primary Examiner* — Dominic J Bologna
(74) *Attorney, Agent, or Firm* — Cantor Colburn LLP

(57) ABSTRACT

A detector apparatus is provided and includes a collector having access to a sample of a gaseous fluid and a tester coupled to and disposed remotely from the collector. The tester includes a test chamber into which a sample is directed from the collector, an excitation element to excite the sample in the test chamber and a spectrum analyzing device coupled to the test chamber to analyze the excited sample for evidence of a concentration of particles of interest in the gaseous fluid exceeding a threshold concentration. The threshold concentration is defined in accordance with a type of the particles of interest and a residence time of the sample.

18 Claims, 6 Drawing Sheets

(51) Int. Cl.

| | |
|---|---|
| *G01N 21/25* | (2006.01) |
| *G01J 3/02* | (2006.01) |
| *B66C 1/10* | (2006.01) |
| *B66C 13/18* | (2006.01) |
| *B66C 19/00* | (2006.01) |
| *G01J 3/443* | (2006.01) |
| *G01N 1/22* | (2006.01) |
| *G01V 5/00* | (2006.01) |
| *G01N 21/64* | (2006.01) |
| *G01N 21/71* | (2006.01) |
| *G06Q 10/08* | (2012.01) |
| *G01N 15/14* | (2006.01) |
| *B64F 1/32* | (2006.01) |
| *B64F 1/36* | (2017.01) |
| *G01N 1/24* | (2006.01) |
| *G01N 15/00* | (2006.01) |

(56) References Cited

U.S. PATENT DOCUMENTS

| | | | |
|---|---|---|---|
| 8,867,687 | B2 | 10/2014 | Bertozzi |
| 8,891,073 | B2 | 11/2014 | Effenberger, Jr. |
| 2006/0018735 | A1* | 1/2006 | Takehara ............... B66C 19/002 414/141.3 |
| 2008/0129994 | A1* | 6/2008 | Murnick ............ G01N 21/1717 356/318 |
| 2009/0040505 | A1* | 2/2009 | Ackerman ............ B01F 5/0619 356/36 |
| 2011/0086415 | A1* | 4/2011 | Tustison ................... D01F 1/09 435/235.1 |
| 2013/0119267 | A1* | 5/2013 | Deshmukh ............. G01N 21/01 250/442.11 |
| 2015/0226637 | A1* | 8/2015 | Sanchez ................. G01M 11/30 385/12 |

OTHER PUBLICATIONS

A Technical Review: The Domestic Nuclear Detection OfficeTransformational and Applied Research Directorate R&D Program; IEEE and APS, Aug. 2013; 62 pages.

Kouzes, Challenges for Interdiction of Nuclear Threats and Borders; IEEE Manuscript; Jun. 2009; 3 pages.

* cited by examiner

RADIOACTIVE ANOMALY DETECTOR

BACKGROUND

The present invention relates to a radioactive anomaly detector and, more particularly, to radioactive anomaly detector for use in identifying illicit active nuclear threats.

A substantial danger to port cities is the importation of storage containers containing weaponized materials such as chemical or biological weapons or special nuclear materials (SNNs) as found in nuclear bombs or dirty bombs. Identifying which storage containers contain those weaponized materials is therefore vital in maintaining a safe society. However, since storage containers and imported and exported goods are integral to healthy commerce, it is not practical to inspect each and every storage container coming into and leaving a port since such inspections would heavily impede commerce.

Current inspection methods include laser induced breakdown spectroscopy (LIBS), active X-Ray detection and passive Gamma Ray detection. A LIBS method is generally suitable only for surface residual testing and works by ablating a surface of a specimen being tested. Thus, LIBS is a specific point screening and cannot cover broad areas or volumes. Active X-Ray detection is used to identify certain materials by exposure of those materials to high levels of X-Rays and is generally suitable only for secondary screening. Passive Gamma Ray detection is extremely sensitive to other X-Ray sources in operation nearby and can be readily defeated by adding small amounts of radiation shielding.

SUMMARY

According to one embodiment of the present invention, a detector apparatus is provided and includes a collector having access to a sample of a gaseous fluid and a tester coupled to and disposed remotely from the collector. The tester includes a test chamber into which a sample is directed from the collector, an excitation element to excite the sample in the test chamber and a spectrum analyzing device coupled to the test chamber to analyze the excited sample for evidence of a concentration of particles of interest in the gaseous fluid exceeding a threshold concentration. The threshold concentration is defined in accordance with a type of the particles of interest and a residence time of the sample.

According to another embodiment, a detector apparatus is provided and includes a collector having access to an interior of a storage container and a tester coupled to the collector and disposed on a frame element configured to manipulate the storage container. The tester includes a test chamber into which a sample of a gaseous fluid drawn from the interior of the storage container by the collector is directed, an excitation element to excite the sample in the test chamber and a spectrum analyzing device coupled to the test chamber to analyze the excited sample for evidence of a concentration of particles of interest in the gaseous fluid exceeding a threshold concentration. The threshold concentration is defined in accordance with a type of the particles of interest and a residence time of the sample in the interior of the storage container.

According to yet another embodiment, a method of operating a detector apparatus is provided and includes directing a sample of a gaseous fluid drawn from an interior of a storage container into a test chamber, lasing the sample in the test chamber to excite the sample, performing spectroscopy on the excited sample, analyzing results of the spectroscopy for evidence of a concentration of particles of interest in the gaseous fluid exceeding a threshold concentration and defining the threshold concentration in accordance with a type of the particles of interest and a residence time of the sample in the interior of the storage container.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

As is described below, an apparatus and method of anomaly detection of hidden (shielded) special nuclear materials (SNM)/smuggled nuclear warheads in shipping containers at ports of entry is provided. The apparatus and method do not require that the shipping containers be opened or that the flow of commerce be otherwise impeded. The concept of the apparatus and method leverages typical shipping transport times to allow for certain isotopes created by the SNMs in the ambient container atmosphere to be built up to detectable concentration levels. Direct line of sight to the SNM via conventional detection techniques is not required, and shielded SNM will readily be detected via these signatures of anomalous elevated molecular isotopic species in and adjacent to the container atmosphere. In this case, a scanning sampler non-invasively collects fugitive emission from near container vents as it is being loaded or unloaded via a crane system or in the case of land-based entry ports, as the trucks move or pass through check points. This sample is routed to a remote or local sensor enclosure that includes an excitation laser and a spectrum analyzing device that measures and analyzes spectra against known signatures in real time for ready identification of anomalously high or elevated isotopic molecular species levels. The measurement time will be in the several seconds time scale.

The above-described apparatus and method is immune to shielding since it looks for atmospheric interaction with the SNMs that generates elevated concentration of isotopic species, relies on build-up of anomalous isotopic species to provide concentration levels much higher (by orders of magnitude) than background and is a truly non-invasive sensing technique with near real time sensing modality.

Figure 1:
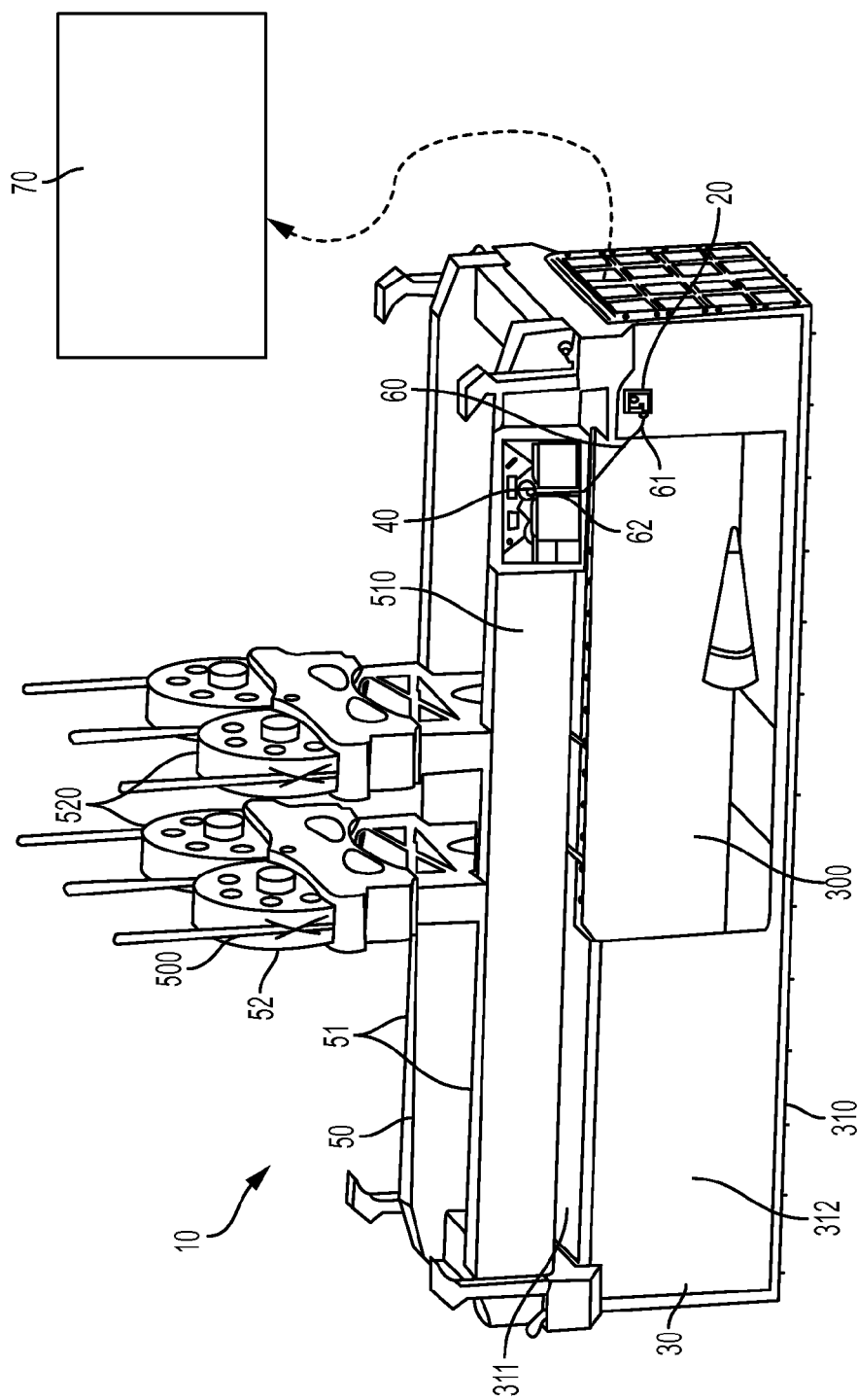
FIG. 1 is a perspective view of a detector apparatus in accordance with embodiments.
Figure 2:
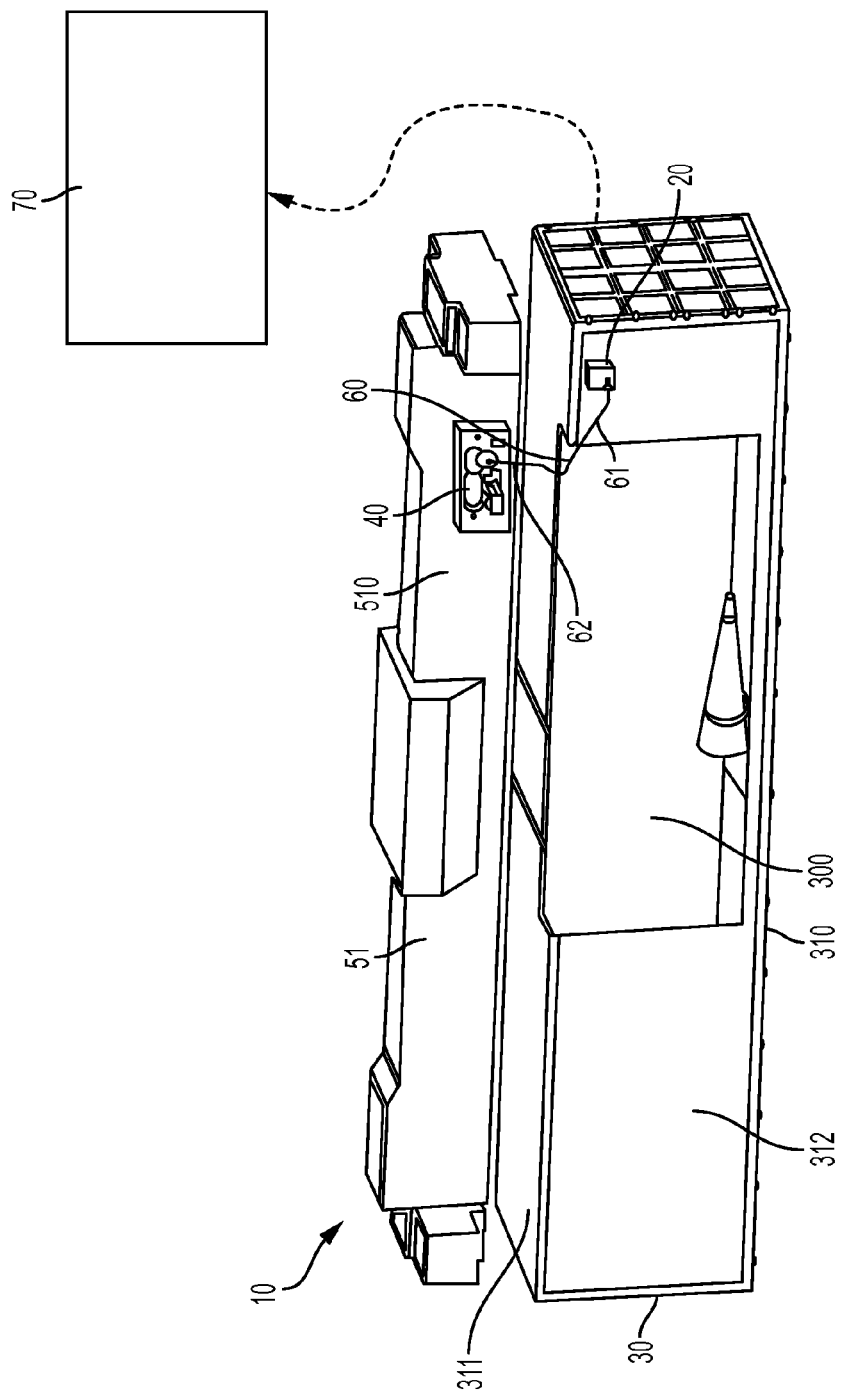
FIG. 2 is a perspective view of a detector apparatus in accordance with alternative embodiments.

With reference to FIGS. 1 and 2, a detector apparatus 10 is provided. The detector apparatus 10 includes a collector 20, a tester 40, a blower 42 that may be a component of the collector 20 or the tester 40 and a hose 60. The collector 20 has access to an interior 300 of the storage container 30. The tester 40 is coupled to the collector 20 and disposed on a frame element 50. The frame element 50 is disposed and configured to manipulate the storage container 30. The hose 60 has first and second opposite ends 61 and 62 and is coupled at the first end 61 to the collector 20 and at the second end 62 to the tester 40.

As shown in FIG. 1, the storage container 30 may be provided as an iso-or intermodal container that has a base 310, a top 311 and sidewalls 312 that cooperatively define the interior 300. In any case, the storage container 30 may be employed to ship loads overseas on trips that could last anywhere from a few hours to a few weeks. The frame element 50 is generally provided in port and may be provided as a component of a crane 500 that is disposed and configured to manipulate the storage container 30 by lifting and transferring the storage container 30 from one location to another (e.g., from on-board a cargo ship to a warehouse on-shore). The manipulation of the storage container 30 by the frame element 50 may last from a few (or several) seconds to a few minutes.

In accordance with embodiments, the frame element 50 may include one or more rails 51 and one or more lifting/transferring assemblies 52. The one or more rails 51 are attachable to the storage container 30 and include at least one rail-face 510. The lifting/transferring assemblies 52 are coupled to portions of the one or more rails 51 and can be provided as a pulley system 520 or some other suitable pneumatic or hydraulic system. In accordance with alternative embodiments and, as shown in FIG. 2, at least one or more components of the frame element 50 may be disposed in a warehouse or main distribution center.

Figure 3A:
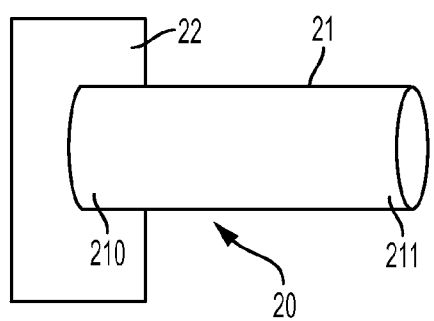
FIG. 3A is a side view of a collector of the detector apparatus of FIG. 1 or 2 in accordance with embodiments.
Figure 3B:
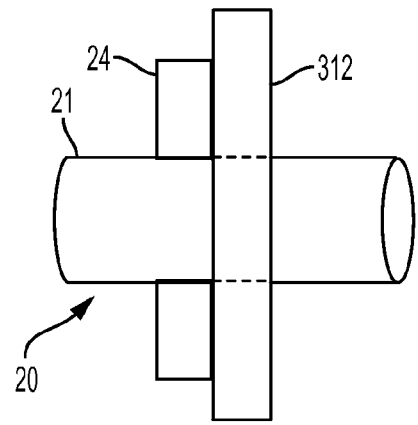
FIG. 3B is a side view of a collector of the detector apparatus of FIG. 1 or 2 in accordance with alternative embodiments.
Figure 3C:
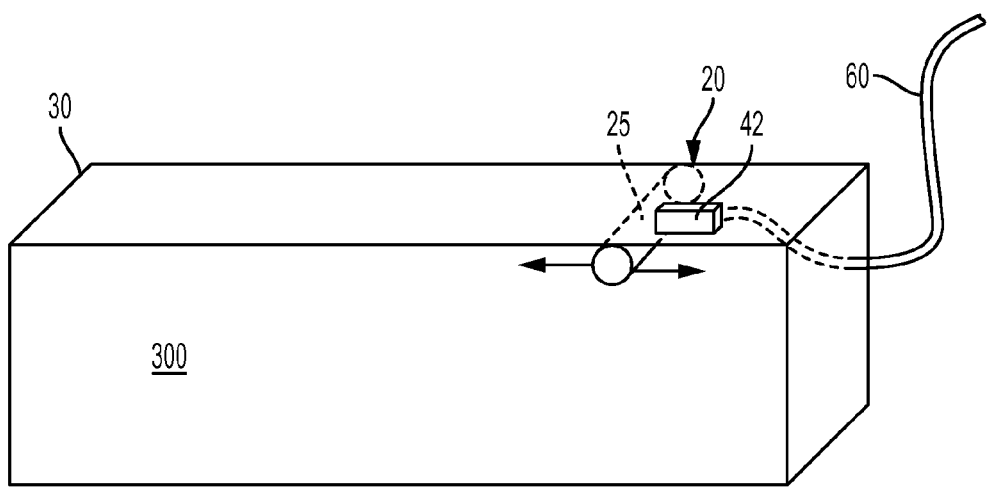
FIG. 3C is a perspective view of a collector of the detector apparatus of FIG. 1 or 2 in accordance with alternative embodiments.

With reference to FIGS. 3A, 3B and 3C, the collector 20 may be coupled to one or more of the base 10, the top 311 or the sidewalls 312 of the storage container 30 and has access to the interior 300. Such access may be enabled by way of at least one or more of vent sampling, direct sampling and diffuse sampling. As shown in FIG. 3A, the collector 20 may include a body 21, at least one shroud 22 that covers a vent on the storage container 30 and possibly a second shroud that provides for positive pressure assistance. The body 21 is formed to define an inlet 210, an outlet 211, which is coupled to the first end 61 of the hose 60, and an interior pathway from the inlet 210 to the outlet 211. In a vent sampling operation, the shroud 22 pulls a sample from air vented from the interior 300 and directs the sample into the inlet 210 whereby the sample travels along the interior pathway to the outlet 211 and the hose 60.

As shown in FIG. 3B, the collector 20 may include the body 21 and a flange 24. The flange 24 is coupled to the body 21 and is attachable to the storage container 30 as a support for the body 21. In a direct sampling operation, which requires minimal positioning finesse, the body 21 is disposed to puncture a sidewall 312 of the storage container 30 to acquire a flowpath for air to proceed from the interior 30 to the hose 60. The body 21 may be configured to self-seal the puncture upon completion of the sampling.

As shown in FIG. 3C, the collector 20 may include a duct 25 that is coupled to the hose 60 and is disposable on an exterior of the storage container 30 or in the interior 300. In either case, in a diffuse sampling operation, the duct 25 sweeps transversely across a section of the storage container 30. The duct 25 thereby pulls a sample as it traverses the section and may be assisted in this regard by a positive or negative pressure device.

Figure 4:
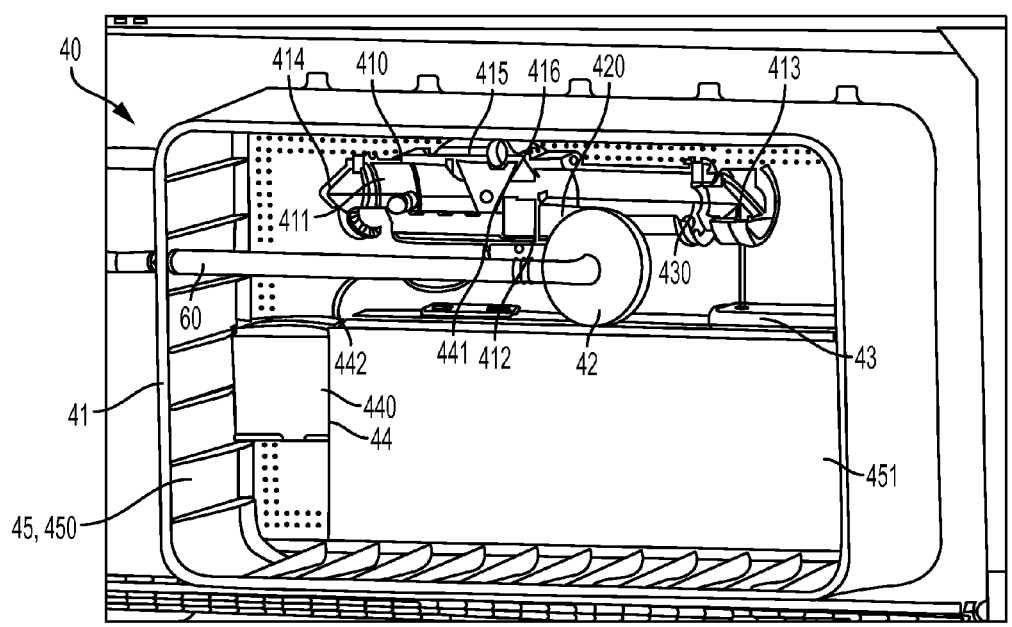
FIG. 4 is a perspective view of a tester of the detector apparatus of FIG. 1.
Figure 5:
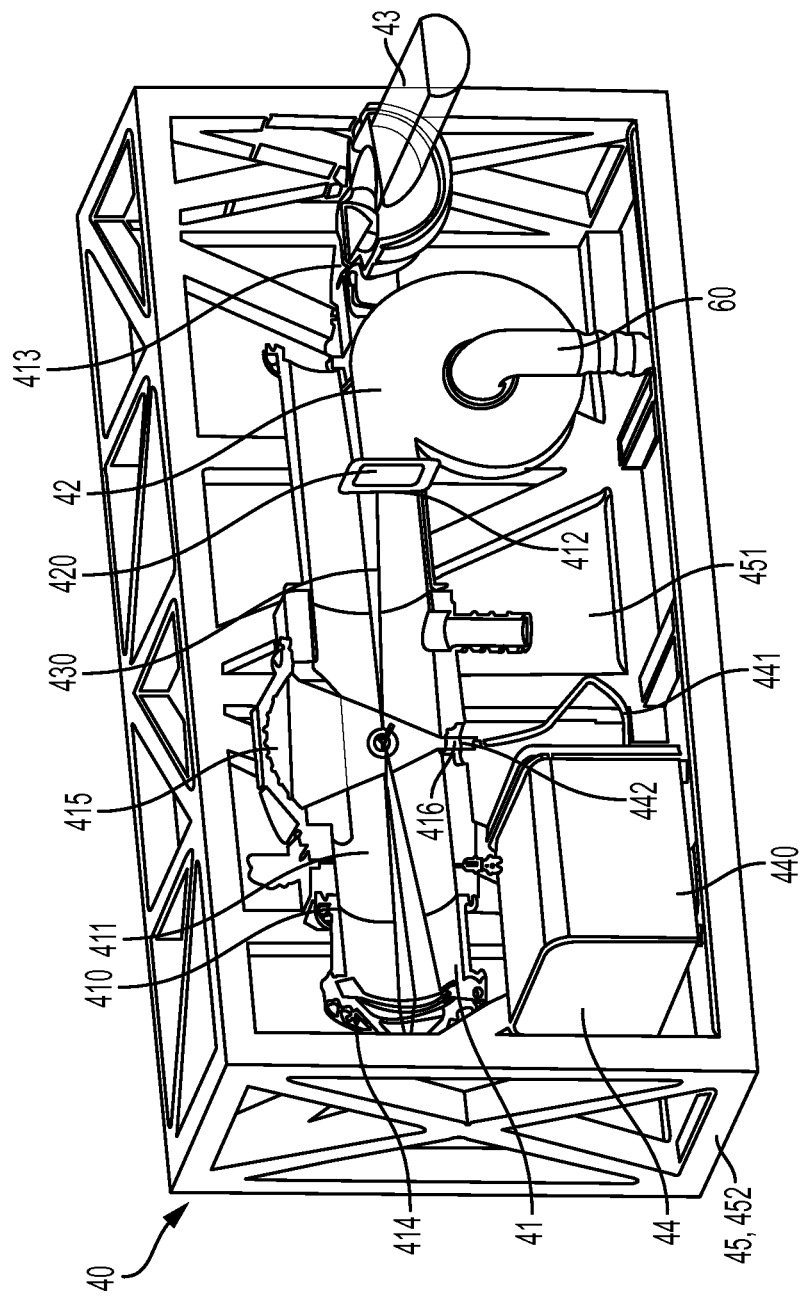
FIG. 5 is a perspective view of a tester of the detector apparatus of FIG. 2.

With reference to FIGS. 4 and 5, the tester 40 includes a test chamber 41, the above-mentioned blower 42 in some cases, an excitation element 43, a spectrum analyzing device 44 and an enclosure 45 to house at least one of the test chamber 41, the blower 42, the excitation element 43 and the spectrum analyzing device 44. In accordance with embodiments and, as shown in FIG. 4, the enclosure 45 may be provided as a first solid rectangular body 450 defining a tester interior 451 with generally solid, opaque walls that are penetrated by the hose 60. In accordance with alternative embodiments and, as shown in FIG. 5, the enclosure 45 may be provided as a second solid rectangular body 452 with generally solid but open tress-type wall features.

The test chamber 41 may be provided as a tubular body 410 that is formed to define an elongate interior 411. The tubular body 410 has an opening 412 that is accessible by the blower 42 and may include at least one reflective surface 413 and at least one absorptive surface 414. The test chamber 41 may further include a central portion 415 and an aperture 416. The central portion 415 bulges outwardly (see, e.g., FIG. 5) in a convex configuration relative to an outer surface of the remainder of the tubular body 410 and the aperture 416 provides for optical or sensor access to the portion of the elongate interior 411 corresponding to the central portion 415. The test chamber 41 may further include additional parabolic collecting/focusing optical elements at the central portion 415 to improve a performance capability of the test chamber 41.

The blower 42 may be provided as a fan or a compressor and is coupled to the second end 62 of the hose 60. The blower 42 is thus configured as an air moving element capable of generating airflow through the hose 60. Such airflow encourages the sample to be pulled from the interior 300 of the storage container 30 by the collector 20. The blower 42 includes an outlet 420 that is disposed and configured to direct the sample pulled from the interior 300, which may generally be a gaseous fluid, such as air, into the elongate interior 411 of the test chamber 41 by way of the opening 412.

While the blower 42 is illustrated in FIGS. 4 and 5 as being housed within the tester 40, it will be understood that alternative embodiment exist. For example, the blower 42 may also be provided as a component of the collector 20. In such cases and, as shown in FIG. 3C, the blower 42 may be disposed between the duct 25 and the hose 60 such that the blower 42 is positioned to pull fluid into the duct 25 and the drive such fluid from the duct 25 into the hose 60.

The excitation element 43 may be provided as a device that generates a laser beam 430 or another similar feature. The excitation element 43 is therefore disposed and configured to direct the laser beam 430 into the elongate interior 411 of the test chamber 41 to thereby excite the sample in the elongate interior 411. In accordance with embodiments and, as shown in FIGS. 1 and 4, the excitation element 43 may be mounted within the tester interior 451 at an offset from the test chamber 41. In operation, the excitation element 43 emits an eye-safe concentrated laser beam 430 of light (e.g., an ultra-fast laser beam at 1550 nm) toward the at least one reflective surface 413, which redirects the laser beam 430 into and along a longitudinal axis of the elongate interior 411 so that the laser beam 430 terminates at the at least one absorptive surface 414. The at least one reflective surface 413 may have a focusing curvature that focuses the laser beam 430 at a predefined point within the portion of the elongate interior 411 corresponding to the central portion 415. Alternatively, the at least one reflective surface 413 may direct the laser beam 430 through an additional optical lens that focuses the laser beam 430 at the predefined point within the portion of the elongate interior 411 corresponding to the central portion 415.

In accordance with alternative embodiments and, as shown in FIGS. 2 and 5, the excitation element 43 may be mounted on a rigid surface of the main distribution center at an exterior of the tester 40. In operation, the excitation element 43 emits an eye-safe concentrated laser beam 430 of light (e.g., an ultra-fast laser beam at 1550 nm) through the tress-type wall features of the second solid rectangular body 452 and toward the at least one reflective surface 413. As above, the at least one reflective surface 413 then redirects the laser beam 430 into and along the longitudinal axis of the elongate interior 411 so that the laser beam 430 terminates at the at least one absorptive surface 414. Again, the at least one reflective surface 413 may have a focusing curvature that focuses the laser beam 430 at a predefined point within the portion of the elongate interior 411 corresponding to the central portion 415 or the at least one reflective surface 413 may direct the laser beam 430 through an additional optical lens that focuses the laser beam 430 at the predefined point within the portion of the elongate interior 411 corresponding to the central portion 415.

The focusing of the laser beam 430 at the predefined point within the portion of the elongate interior 411 corresponding to the central portion 415 causes the sample directed into the elongate interior 411 by the blower 42 to become excited and to generate in the excited state a plasma ball or filaments. The spectrum analyzing device 44 is coupled to the test chamber 41 and is disposed and configured to analyze the plasma ball/filaments of the excited sample for evidence of a concentration of particles of interest in the gaseous fluid of the sample exceeding a threshold concentration. The threshold concentration is defined in accordance with a type of the particles of interest and a residence time of the sample in the interior of the storage container 30.

In accordance with embodiments, the spectrum analyzing device 44 may be provided as a spectroscopy device, a spectrometer or a spectrophotometer. In the latter case, the spectrum analyzing device 44 analyzes and resolves a spectrum of a signal and also measures its fluorescence strength, emittance and intensity. In any case, the spectrum analyzing device 44 may include a computing device 440, a fiber optic sensor 441 and a fiber optic cable 442 by which the fiber optic sensor 441 is coupled to the computing device 440. The fiber optic sensor 441 is disposable or mountable in the aperture 416 to optically sense the generated plasma ball/filaments in the elongate interior 411 and is configured to generate an optical signal reflective of the optical sensing. This optical signal is transmittable along the fiber optic cable 442 to the computing device 440, which is receptive of the optical signal and configured to perform the analysis for the evidence of a concentration of particles of interest in the gaseous fluid of the sample exceeding a threshold concentration.

In accordance with embodiments, the detector apparatus 10 may be designed to identify whether a given storage container 30 is at a high risk for transporting a weaponized object such as a load containing a chemical or biological weapon, weapons grade nuclear material or a nuclear weapon (for the sake of clarity and brevity, the following description will relate to the case of the storage container being used to transport a nuclear weapon). In the case of the storage container 30 containing weapons grade nuclear material or a nuclear weapon, the load in the storage container 30 may include surreptitiously transported SNMs that are prone to SNM radiation leakages that cannot be easily sealed with hermetic sealing. Such SNM radiation leakages lead to the presence of an increased incidence of isotopic molecular by-products of the interaction of the leaked SNM radiation with the air inside the interior 300 of the storage container 30. The isotopic molecular by-products may include, but are not limited to, at least one or more of DHO, $^{14}CO$, $^{14}CO_2$ and $H^{36}Cl$.

As an example, if the storage container 30 is used to transport a typical low yield plutonium weapon, the plutonium may have a neutron emission rate of about $4 \times 10^5$ n/s. Neutron activation kinetics will then produce isotopic molecular species in an ambient sea fairing atmosphere within the interior 300 in accordance with $^{14}N+n \rightarrow {}^{14}C+p$ and $^{35}Cl(n,\gamma)^{36}Cl$ where it is understood that $^{14}C$ and $^{36}Cl$ have natural abundances of about 1 part per trillion and energetic chemical dynamics of newly created isotopes results in preferential chemical bonding. That is, $^{14}CO$ in the case of $^{14}C$ and $H^{36}Cl$ in the case of $^{36}Cl$. While a natural steady state background concentration of $^{14}CO$ in the atmosphere is about 6-10 molecules per $cm^3$ (with $H^{36}Cl$ native background concentration expected to be even lower since the molecule is shorter lived), their respective concentrations in the shipping container 30 will be significantly higher. That is, for a volume $40 \times 8 \times 8$ cubic feet, within a few days $^{14}CO$ concentration can build up to as high as about 8000 molecules per $cm^3$ depending on diffusion, convective flow, etc.

In operation, the spectrum analyzing device 44 analyzes the excited sample for evidence of a concentration of isotopic molecules in the gaseous fluid of the sample. In detail, the computing device 440 of the spectrum analyzing device 44 analyzes the spectrum of the excited sample for evidence that the concentration of the isotopic molecules noted above exceed a threshold concentration. This threshold concentration may be defined for the particular isotopic molecules being searched for based on the residence time of the sample in the interior 300 of the storage container 30. That is, first and second threshold concentrations may be respectively defined for $^{14}CO$ and for $H^{36}Cl$ based on an amount of time the storage container 30 took from its departure port to its destination. Thus, the first and second threshold concentrations may be increased for each isotopic molecule for longer journeys (e.g., weeks or at least several days).

In addition and, in accordance with further embodiments, the threshold concentration may be adjusted to achieve a certain maximum number of false positive results (e.g., 1 in 10,000). In such cases, since false positive readings may result in the storage container 30 being inspected further over an extended period of time and at cost, the threshold concentration may be increased if it is found that the spectrum analyzing device 44 gives an excessive number of false positive readings that have an unacceptable impact upon commerce. Moreover, it is to be understood that the computing device 440 of the spectrum analyzing device 44 can be programmed or attuned to search for multiple isotopic molecules at once and/or to search for chemical signatures of radiological, biological and/or chemical weapons.

From published neutron signatures of a nuclear device, an estimate of expected isotope concentration of $^{14}CO$ built up in a typical shipping container after a few days can be as high $10^4$ molecules per $cm^3$ which provides for orders of magnitude levels above background. Although the sample concentration may become diluted depending on, e.g., convection currents, mixing with outside atmosphere and negligible cosmic neutron interference, the detector apparatus 10 can be effective in use with as little as about 100 molecules per $cm^3$ (which is still 10 times more than background) with less than 1 second of measurement time.

Figure 6:
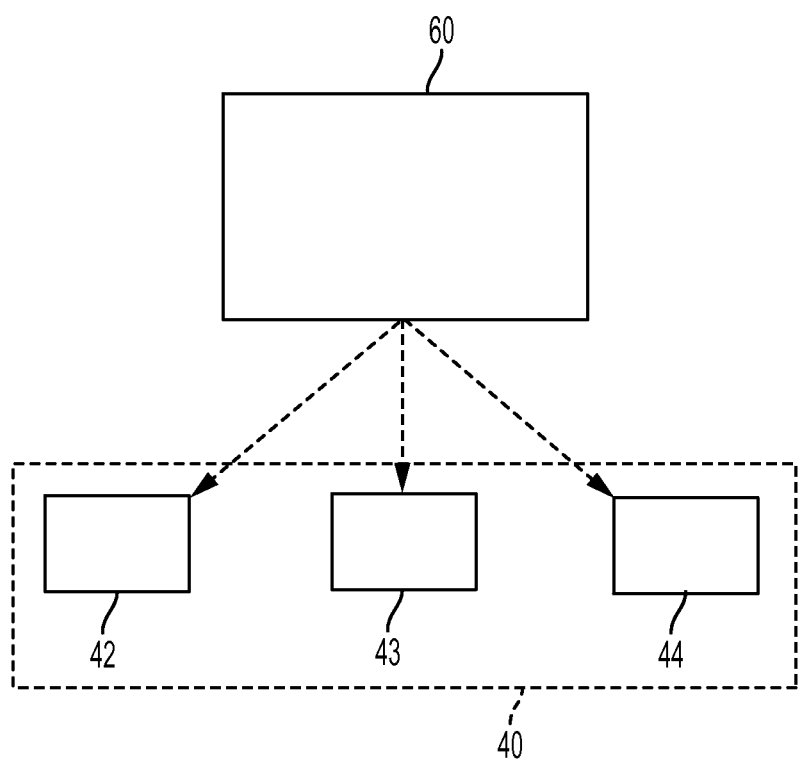
FIG. 6 is a schematic diagram of a controller of the detector apparatuses of FIGS. 1 and 2 in accordance with embodiments.

With reference to FIGS. 1, 2 and 6, the detector apparatus 10 of FIG. 1 or 2 may further include a controller 60 and a secondary screening system 70. The controller 60 is operably coupled to the tester 40 and configured to control the blower 42, the excitation element 43 and the spectrum analyzing device 44 and to analyze the evidence for identification of a suspect reading. In particular, the controller 60 may control the blower 42 to direct multiple samples of the gaseous fluid into the test chamber 41. The controller 60 may further control the excitation element 43 to excite each of the multiple samples within the test chamber 41 sequentially and may further control the spectrum analyzing device 44 to analyze each of the multiple excited samples in turn. The secondary screening system 70 is provided whereby storage containers associated with identifications of suspect readings by the controller 60 are routable for secondary or more extensive screening operations.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The described embodiments were chosen and described in order to best explain the principles of the invention and the practical application, and to enable others of ordinary skill in the art to understand the invention for various embodiments with various modifications as are suited to the particular use contemplated.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

What is claimed is:

1. A detector apparatus, comprising:
a collector having access to a sample of a gaseous fluid in a storage container; and
a tester coupled to and disposed remotely from the collector, the tester comprising:
a test chamber into which the sample is directed from the collector;
an excitation element to excite the sample in the test chamber; and
a spectrum analyzing device coupled to the test chamber to analyze the excited sample for evidence of a concentration of particles of interest in the gaseous fluid exceeding a threshold concentration,
the threshold concentration being defined in accordance with a type of the particles of interest and a residence time of the sample in the storage container prior to an accessing of the sample by the collector, and
wherein the spectrum analyzing device analyzes the excited sample for evidence of a concentration of isotopic molecules in the gaseous fluid exceeding a threshold concentration defined for the isotopic molecules based on the residence time of the sample which is defined as a total amount of time the sample is resident in the storage container prior to the accessing of the sample by the collector.

2. The detector apparatus according to claim 1, further comprising a hose coupled at opposite ends thereof to the collector and the tester.

3. The detector apparatus according to claim 1, wherein the tester further comprises an enclosure to house at least one of the test chamber, the excitation element, and the spectrum analyzing device.

4. The detector apparatus according to claim 1, wherein the test chamber comprises a tubular body having at least one reflective surface and at least one absorptive surface.

5. The detector apparatus according to claim 1, further comprising a blower to direct the sample from the collector to the test chamber.

6. The detector apparatus according to claim 1, wherein the excitation element comprises a laser.

7. The detector apparatus according to claim 6, wherein the laser is mounted within an interior of the tester.

8. The detector apparatus according to claim 6, wherein the laser is mounted externally with respect to the tester.

9. The detector apparatus according to claim 1, wherein the isotopic molecules comprise at least one or more of DHO, $^{14}CO$, $^{14}CO_2$ and $H^{36}Cl$.

10. A detector apparatus, comprising:
a collector having access to an interior of a storage container; and
a tester coupled to the collector and disposed on a frame element configured to manipulate the storage container, the tester comprising:
a test chamber into which a sample of a gaseous fluid drawn from the interior of the storage container by the collector is directed;
an excitation element to excite the sample in the test chamber; and
a spectrum analyzing device coupled to the test chamber to analyze the excited sample for evidence of a concentration of particles of interest in the gaseous fluid exceeding a threshold concentration,
the threshold concentration being defined in accordance with a type of the particles of interest and a residence time of the sample in the interior of the storage container prior to the sample being drawn out from the interior by the collector, and wherein the spectrum analyzing device analyzes the excited sample for evidence of a concentration of isotopic molecules in the gaseous fluid exceeding a threshold concentration defined for the isotopic molecules based on the residence time of the sample which is defined as a total amount of time the sample is resident in the storage container prior to the accessing of the sample by the collector.

11. The detector apparatus according to claim 10, wherein the storage container comprises an intermodal container.

12. The detector apparatus according to claim 11, wherein the collector has access to the interior by way of at least one or more of vent sampling, direct sampling and diffuse sampling.

13. The detector apparatus according to claim 10, wherein the frame element comprises a crane.

14. The detector apparatus according to claim 10, further comprising a controller operably coupled to the tester and configured to control the excitation element and the spectrum analyzing device and to analyze the evidence for identification of a suspect reading.

15. The detector apparatus according to claim 14, wherein the controller controls a blower to direct multiple samples of the gaseous fluid into the test chamber, the excitation element to excite each of the multiple samples and the spectrum analyzing device to analyze each of the multiple excited samples.

16. The detector apparatus according to claim 14, wherein storage containers associated with identifications of suspect readings are routed for secondary screenings.

17. A method of operating a detector apparatus, the method comprising:
   directing a sample of a gaseous fluid drawn from an interior of a storage container into a test chamber;
   lasing the sample in the test chamber to excite the sample;
   performing spectroscopy on the excited sample;
   analyzing results of the spectroscopy for evidence of a concentration of particles of interest in the gaseous fluid exceeding a threshold concentration; and
   defining the threshold concentration in accordance with a type of the particles of interest and a residence time of the sample in the interior of the storage container prior to the sample being drawn out from the interior by the collector,
   wherein the analyzing comprises analyzing the results for evidence of a concentration of isotopic molecules in the gaseous fluid exceeding a threshold concentration defined for the isotopic molecules based on the residence time of the sample in the interior of the storage container which is defined as a total amount of time the sample is resident in the storage container prior to the accessing of the sample by the collector.

18. The method according to claim 17, wherein the isotopic molecules comprise at least one or more of DHO, $^{14}CO$, $^{14}CO_2$ and $H^{36}Cl$.

* * * * *